United States Patent
Nagale et al.

(10) Patent No.: US 10,716,620 B2
(45) Date of Patent: Jul. 21, 2020

(54) EXPANDABLE BALLOON MAPPING AND ABLATION DEVICE

(71) Applicant: Boston Scientific Scimed, Inc., Maple Grove, MN (US)

(72) Inventors: Sandra Nagale, Bolton, MA (US); Mark W. Boden, Harrisville, RI (US); Bryan Allen Clark, Forest Lake, MN (US); Shibaji Shome, Arden Mills, MN (US); Amedeo J. Chiavetta, Derry, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 390 days.

(21) Appl. No.: 15/227,767

(22) Filed: Aug. 3, 2016

(65) Prior Publication Data
US 2017/0035496 A1 Feb. 9, 2017

Related U.S. Application Data

(60) Provisional application No. 62/201,519, filed on Aug. 5, 2015.

(51) Int. Cl.
| | |
|---|---|
| A61B 18/14 | (2006.01) |
| A61B 5/00 | (2006.01) |
| A61B 5/0488 | (2006.01) |
| A61B 5/20 | (2006.01) |
| A61N 1/05 | (2006.01) |

(Continued)

(52) U.S. Cl.
CPC ...... *A61B 18/1492* (2013.01); *A61B 5/04882* (2013.01); *A61B 5/202* (2013.01); *A61B 5/6853* (2013.01); *A61B 18/1485* (2013.01); *A61N 1/0514* (2013.01); *A61N 1/36007* (2013.01); *A61B 2017/00022* (2013.01); *A61B 2017/00044* (2013.01); *A61B 2017/00053* (2013.01); *A61B 2018/0022* (2013.01); *A61B 2018/00178* (2013.01); *A61B 2018/00267* (2013.01); *A61B 2018/00517* (2013.01); *A61B 2018/00577* (2013.01); *A61B 2018/00642* (2013.01); *A61B 2018/00839* (2013.01); *A61B 2018/1467* (2013.01); *A61B 2018/1475* (2013.01)

(58) Field of Classification Search
CPC .. A61B 5/0422; A61B 18/1492; A61B 5/6853
See application file for complete search history.

(56) References Cited

U.S. PATENT DOCUMENTS

| | | | | |
|---|---|---|---|---|
| 5,311,866 A | * | 5/1994 | Kagan | A61B 5/042 29/872 |
| 5,345,936 A | * | 9/1994 | Pomeranz | A61B 5/0422 600/374 |

(Continued)

FOREIGN PATENT DOCUMENTS

| | | |
|---|---|---|
| JP | 2015112114 | 6/2015 |
| WO | 9732532 A1 | 9/1997 |

(Continued)

*Primary Examiner* — Lee S Cohen

(57) ABSTRACT

The present disclosure relates to the field of tissue mapping and ablation. Specifically, the present disclosure relates to expandable medical devices for identifying and treating local anatomical abnormalities within a body lumen. More specifically, the present disclosure relates to systems and methods of focal treatment for overactive bladders.

14 Claims, 6 Drawing Sheets

(51) Int. Cl.
*A61N 1/36* (2006.01)
*A61B 18/00* (2006.01)
*A61B 17/00* (2006.01)

(56) References Cited

U.S. PATENT DOCUMENTS

| | | | | |
|---|---|---|---|---|
| 5,702,438 | A * | 12/1997 | Avitall | A61B 18/1492 600/374 |
| 6,142,993 | A * | 11/2000 | Whayne | A61B 18/1492 600/374 |
| 6,163,716 | A * | 12/2000 | Edwards | A61B 5/0422 128/898 |
| 6,692,490 | B1 * | 2/2004 | Edwards | A61B 18/1477 606/41 |
| 8,467,863 | B2 * | 6/2013 | Kahlert | A61B 5/0422 600/510 |
| 9,011,430 | B2 * | 4/2015 | Habib | A61B 17/22 606/27 |
| 9,265,459 | B2 * | 2/2016 | Nagale | A61B 5/6852 |
| 9,492,113 | B2 * | 11/2016 | Nagale | A61B 5/205 |
| 2006/0069417 | A1 | 3/2006 | Farley et al. | |
| 2007/0265617 | A1 | 11/2007 | Falkenstein et al. | |
| 2013/0030425 | A1 | 1/2013 | Stewart et al. | |
| 2013/0090648 | A1 * | 4/2013 | Nagale | A61B 5/6852 606/41 |
| 2013/0231658 | A1 | 9/2013 | Wang et al. | |
| 2014/0378967 | A1 | 12/2014 | Willard et al. | |
| 2015/0057519 | A1 * | 2/2015 | Ben-David | A61B 5/6853 600/373 |

FOREIGN PATENT DOCUMENTS

| | | |
|---|---|---|
| WO | 0051511 A1 | 9/2000 |
| WO | 2010018569 A1 | 2/2010 |
| WO | 2012086492 | 12/2010 |
| WO | 2011055143 A2 | 5/2011 |

* cited by examiner

EXPANDABLE BALLOON MAPPING AND ABLATION DEVICE

CROSS-REFERENCE TO RELATED APPLICATIONS

This application claims priority to U.S. Provisional Application Ser. No. 62/201,519, filed on Aug. 5, 2015, the entire disclosure of which is herein incorporated by reference.

FIELD

The present disclosure relates to the field of tissue mapping and ablation. Specifically, the present disclosure relates to expandable medical devices for identifying and treating local anatomical abnormalities within body lumens, including the bladder. More specifically, the present disclosure relates to systems and methods of focal treatment for an overactive bladder.

BACKGROUND

Overactive bladder is a medical condition that affects more than 50 million people in the United States. Individuals with an overactive bladder typically experience an increase in urge and frequency of urination, and occasionally incontinence. An overactive bladder may result from increased triggering of the sensory pathways involved in normal bladder control. It has been suggested that abnormal bladder activity may result from morphological changes in one or more distinct anatomical areas of the bladder, including the dome, internal sphincter or trigone. For example, localized changes in detrusor muscle morphology resulting from defects at the cellular and multicellular level tend to correlate with pathological changes, e.g., patchy denervation due to increased amounts of connective tissue between muscle bundles, which may contribute to abnormal muscle function on a macroscopic level. These localized defects often manifest as elevated electrical activity within specific tissue regions of the bladder wall. Identifying and treating these localized defects may prevent or eliminate the symptoms of overactive bladder. Current treatments for overactive bladder, such as systemic administration of drugs, nerve stimulation or Botox injections, are applied to the entire bladder rather than specifically targeting local anatomical abnormalities. Because the therapeutic effect eventually wears off, these treatments often need to be repeated multiple times. Unfortunately, overtreatment may lead to urinary retention that requires self-catheterization to void the bladder.

The transient nature of these systemic treatments may be addressed by mapping the tissues of the bladder wall to identify where local bladder abnormalities originate and then specifically targeting therapeutic treatment to those areas. Currently available bladder mapping devices do not conform to the shape of the bladder and cannot reliably establish and/or maintain contact between each of the electrodes and the bladder wall. Proper positioning of the electrodes may be achieved by attaching the electrodes to the surface of a balloon, as described by Drake et al. (BJU International 2005, vol. 95, pp. 1002-1005). However, the interface between the outer surface of the balloon and the bladder wall leads to irritation of the bladder, which tends to result in artifactual electrical measurements.

There is a continued need for systems and methods for identifying local bladder abnormalities and specifically targeting therapeutic treatments to those areas in a minimally invasive manner. Such treatments may provide a permanent therapeutic effect without increasing the duration of the medical procedure.

SUMMARY

Particular embodiments of the disclosure are described in the Summary and Detailed Description of the Preferred Embodiments, below. Although the disclosure has been described in connection with specific embodiments, it should be understood that the disclosure as claimed should not be unduly limited to such specific embodiments.

The present disclosure relates generally to electrode-bearing mapping and ablation systems that provide enhanced electrical connection with the bladder wall, while at the same time reducing or eliminating artifactual electrical measurements resulting from tissue irritation.

In one aspect, the present disclosure relates to a medical device, comprising: a balloon configured to move between a collapsed configuration and an expanded configuration; a plurality of electrodes carried about an outer surface of the balloon; and a spacer disposed between the surface of the balloon and each of the plurality of electrodes. The electrodes may include sensing electrodes, mapping electrodes, stimulating electrodes and/or ablation electrodes. Alternatively or in addition, each spacer may include a pressure sensor configured to provide pressure feedback when the electrode is in contact with the bladder wall. An individual pressure sensor may be used for each individual spacer, such that pressure feedback information is obtained for each electrode. The balloon may be a non-compliant balloon that expands to a pre-determined maximum volume, but does not expand (i.e., over-expand) beyond that maximum volume. The balloon may comprise a polymer selected from the group consisting of PEBAX, PET, PEN, PBT, PEEK, Hytrel, polyurethane and nylon. A spacer may be bonded to the outer surface of the balloon. Each of the plurality of electrodes may extend outward from the outer surface of the balloon. Each of the plurality of electrodes may be disposed equidistantly about the outer surface of the balloon. Each of the plurality of electrodes may be electrically coupled to an ablation energy source. Each of the plurality of electrodes may be electrically coupled to an electrical activity processing system. The electrical activity processing system may be configured to measure intrinsic electrical activity. At least a portion of the balloon may be fluid permeable. The balloon may conform to the shape of a body lumen when in the expanded configuration. Each electrode of the plurality of electrodes may contact a wall of the body lumen when the balloon is in the expanded configuration. The outer surface of the balloon may not substantially contact a wall of the body lumen when in the expanded configuration. A lumen of the balloon may be in fluid communication with a fluid source, such that the balloon moves from a collapsed configuration to an expanded configuration by flowing a fluid from the fluid source into the lumen of the balloon.

In another aspect, the present disclosure relates to a medical device comprising: a balloon configured to move between a collapsed configuration and an expanded configuration; an expandable-collapsible framework disposed about an outer surface of the balloon; and a plurality of electrodes carried about an outer surface of the framework. The framework may be free-floating about the surface of the balloon. A distal end of the framework may be attached to a distal end of the balloon. The plurality of electrodes may serve as sensing electrodes, mapping electrodes, stimulating electrodes and/or ablation electrodes. Each of the plurality of electrodes may extend outward from the surface of the framework. The plurality of electrodes are disposed equidistant about the surface of the framework. A spacer may be disposed between the outer surface of the framework and each of the plurality of electrodes. The balloon may comprises a compliant polymer selected from the group consisting of silicone rubbers, polyurethanes, butyl rubbers, latexes, styrene-isobutylene-styrene block copolymers and EPDM. The balloon may be formed of a non-electrically conductive material. Each of the plurality of electrodes may be electrically coupled to an ablation energy source. Each of the plurality of electrodes may be electrically coupled to an electrical activity processing system, including, for example, an electromyograph. The electrical activity processing system may be configured to measure intrinsic electrical activity. A lumen of the balloon may be in fluid communication with a fluid source, such that the balloon moves from a collapsed configuration to the expanded configuration by flowing a fluid from the fluid source into the lumen of the balloon. At least a portion of the balloon may be fluid permeable. The framework may conform to the shape of a body lumen when the balloon is in the expanded configuration. Each the plurality of electrodes on the surface of the framework may contact a wall of the body lumen when the balloon is in the expanded configuration. The outer surface of the balloon may not substantially contact a wall of the body lumen when the balloon is in the expanded configuration.

In another aspect, the present disclosure provides a method of introducing a medical device into a body lumen, wherein the medical device includes: a balloon configured to move between a collapsed configuration and an expanded configuration; an expandable-collapsible framework disposed about an outer surface of the balloon; and a plurality of electrodes carried about an outer surface of the framework; moving the balloon from a collapsed configuration to an expanded configuration such that the electrodes carried about the surface of the balloon contact a tissue of the body lumen; measuring electrical activity within the tissue of the body lumen in contact with each of the electrodes; identifying each electrode that detected an elevated electrical activity within the tissue of the body lumen; and applying electrical energy to each electrode that identified elevated electrical activity. The body lumen may be the lumen of a bladder. Applying the electrical energy may reduce the elevated electrical activity with the tissue of the body lumen, thereby reducing at least one symptom of an overactive bladder.

In another aspect, the present disclosure provides a method of introducing a medical device into a body lumen, wherein the medical device includes: a balloon configured to move between a collapsed configuration and an expanded configuration; an expandable-collapsible framework disposed about an outer surface of the balloon; and a plurality of electrodes carried about an outer surface of the framework, moving the balloon from a collapsed configuration to an expanded configuration such that the electrodes carried about the surface of the framework contact a tissue of the body lumen; measuring electrical activity within the tissue of the body lumen in contact with each of the electrodes; identifying each electrode that detected an elevated electrical activity within the tissue of the body lumen; and applying electrical energy to each electrode that identified elevated electrical activity. The body lumen may be the lumen of a bladder. Applying the electrical energy may reduce the elevated electrical activity with the tissue of the body lumen, thereby reducing at least one symptom of an overactive bladder.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to systems and methods for mapping and ablating overactive tissue(s) within the bladder, it should be appreciated that the present disclosure may be applicable to mapping and ablating a variety of organs, including, for example, the gastro-intestinal (GI) tract, stomach (e.g., irritable bowel disease, cancer, obesity etc.), uterus (e.g., fibroids, uterine bleeding etc.) esophagus and vascular system.

As used herein, the term "distal" refers to the end farthest away from a medical professional when introducing a device into a patient, while the term "proximal" refers to the end closest to the medical professional when introducing a device into a patient.

As used herein, "expandable" or "expanded" refers to an increase in diameter, as compared to the diameter in a "collapsible" or "collapsed" configuration. As used herein, "diameter" refers to the distance of a straight line extending between two points and does not necessarily indicate a particular shape.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

Figure 1:
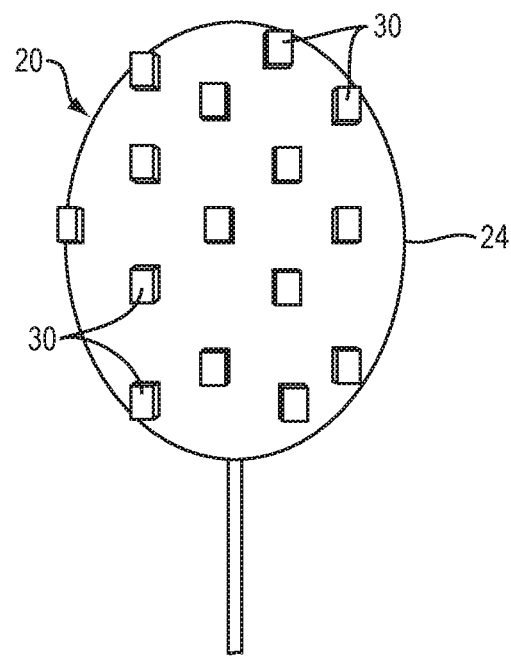
FIG. 1 is a side view of a balloon with attached electrodes, according to an embodiment of the present disclosure.

FIG. 1 provides a schematic view of a medical device that includes an inflatable balloon 20 with attached electrodes 30 for mapping and ablating the tissues of the bladder wall. The balloon 20 is configured to be inserted through the urethra into the bladder of the patient in a collapsed (i.e., deflated or non-expanded) configuration. Once properly positioned within the bladder, the balloon is moved to an expanded (i.e., inflated) configuration such that the electrodes 30 disposed about the outer surface 24 of the balloon 20 are placed in contact with the tissues of the bladder wall. In one embodiment, each electrodes includes a course (i.e., rough) surface to improve and maintain contact with the bladder wall. Any number of electrodes 30 may be disposed about the outer surface 24 of the balloon 20 to electrically map the tissues of the bladder wall. For example, there may be one, two, three, four, five, six, seven, eight, nine, ten, eleven, twelve, sixteen, twenty, twenty-four, or more electrodes. The electrodes may be also of different shapes and sizes. To ensure that the entire bladder is mapped in a uniform manner, the electrodes may be disposed equidistantly about the outer surface of the balloon. The electrodes may also be spaced non-uniformly, for example, with greater density at areas like the bladder neck and lower density at the bladder dome where density of receptors is lower.

Figure 2:
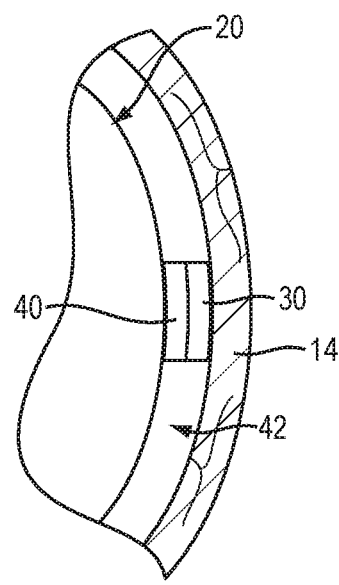
FIG. 2 is a magnified cross-sectional view of an electrode attached to the balloon of FIG. 1.

Referring to FIG. 2, a spacer 40 may be placed between the outer surface 24 of the balloon 20 and each electrode 30 to ensure that the electrodes 30 are raised above and extend outward from the outer surface 24 of the balloon 20. In one embodiment, each spacer 40 may include a pressure sensor configured to provide pressure feedback when the electrode 30 is in contact with the bladder wall. An individual pressure sensor may be used for each individual spacer 40, such that pressure feedback information is obtained for each electrode 30. Beneficial spacer materials include, for example, synthetic polymers and rubbers, metals and metal alloys, shape memory polymers, among others. Spacer thicknesses may range, from 0.1 mm to 100 mm, more typically, from 0.5 mm to 10 mm. In general, the spacers include a width sufficient to raise each electrode approximately 0.5 mm to approximately 1.00 cm above the outer surface of the balloon. Each spacer 40 may be attached to the outer surface 24 of the balloon 20 using, by way of non-limiting example, a glue, a weld, a UV-curable acrylate resin or other suitable adhesive. Alternatively, the spacer may be incorporated as an integral part of the balloon surface during the polymer curing process using the same material used to form the balloon. For example, the thickness of the balloon may be increased outward of the balloon surface at equidistant spots to provide thick areas onto which electrodes are attached/glued. The spacer may also be incorporated as an integral part of the balloon by providing finger-like projections, onto which electrodes are attached/glued, that extend outward from the body of the balloon when in the expanded configuration. Direct contact with balloon surfaces may tend to cause irritation in the tissues of the bladder wall 14, which may lead to inflammation and erroneous electrical activity. As discussed below, the spacers 40 may provide more reliable and accurate mapping of the bladder wall by elevating the respective electrode attached thereto above the outer surface 24 of the balloon 20 to minimize or prevent contact between the outer surface 24 of the expanded balloon and the tissues of the bladder wall 14. The space 42 between the outer surface 24 of the balloon 20 and the bladder wall 14 also allows saline, or other suitable electrically conductive fluid, to be irrigated around the outer surface 24 of the balloon to provide a consistent interface between the bladder wall 14 and each electrode 30. This allows the bladder wall to remain hydrated and provides improved electrical conductivity between the tissues of the bladder wall 14 and each electrode 30 for more reliable detection of intrinsic electrical activity. Once one or more regions of elevated electrical activity have been detected within the tissues of the bladder wall, the electrically conductive fluid further allows for accurate focal delivery of electrical energy (i.e., ablation energy) to the target tissues with minimal ablation of surrounding normal tissue.

The balloon depicted in FIGS. 1-2 may be formed of a flexible material such that it conforms to the shape of the bladder 10 to push each electrode 30 against the bladder wall 14. The non-compliant nature of the balloon ensures that the balloon does not over-expand, thereby maintaining the space 42 for the infused saline to fill. As will be understood by those of skill in the art, a balloon can be formed using any suitable technique, such as blow molding, film molding, injection molding, dip coating and/or extrusion, among others. For example, a polymer tube can be extruded, and can thereafter stretched and blown to form a balloon. Methods of forming a balloon from a polymer tube are described, for example, in commonly-assigned U.S. Ser. No. 10/263,225, filed Oct. 2, 2002, and entitled "Medical Balloon;" Anderson, U.S. Pat. No. 6,120,364; Wang, U.S. Pat. No. 5,714,110; and Noddin, U.S. Pat. No. 4,963,313, all incorporated herein by reference in their entirety.

The balloon may include a combination of elastomeric and non-compliant materials. For example, balloon can include one or more thermoplastics and/or thermosets. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers and silicones. Other examples of thermosets include epoxies and isocyanates. Biocompatible thermosets may also be used. Biocompatible thermosets include, for example, biodegradable polycaprolactone, poly(dimethylsiloxane) containing polyurethanes and ureas and polysiloxanes. Ultraviolet curable polymers, such as polyimides and acrylic or methacrylic polymers and copolymerscan also be used. Other examples of polymers that can be used in balloons include polyethylenes, polyethylene ionomers, polyethylene copolymers, polyetheretherketone (PEEK), thermoplastic polyester elastomers (e.g., Hytrel®) and combinations thereof. The balloon may include multiple layers provided by, for example, co-extrusion. Other polymers are described, for example, in U.S. Pat. Pub. No. 2005/0043679, filed on Aug. 21, 2003, entitled "Medical Balloons," which is incorporated herein by reference.

The lumen of the bladder is typically asymmetrical with a wide range of shapes and sizes depending, for example, on the age and/or size of the individual patient. In one embodiment, consistent electrode contact with the wall of an asymmetrically shaped bladder is achieved using a balloon specifically designed to conform to the shape of an individual patient's bladder. The internal dimensions of a fully expanded bladder are first determined using known medical imaging techniques such as ultrasound, magnetic resonance imaging (MRI), computed radiography (CR) or computerized tomography (CT), among others. A three-dimensional (3-D) mold of the expanded bladder is then formed from wax or using a three-dimensional printer, as is known in the art. A balloon is then formed using the 3-D mold. For example, the mold may be dipped in a silicone solution and allowed to set (e.g., at room temperature for twelve hours). The coated mold is then heated to a temperature and for a time sufficient to cure the silicone (e.g., baked for two hours at 400-450° C. and cooled at room temperature for four hours). The mold is then dissolved and removed, leaving the cured silicone or shape memory polymer body (i.e., balloon). The balloon is rinsed with water, heated (e.g., for thirty minutes at 150° C.) and cooled at room temperature. Spacers and electrodes may then be adhered to the outer surface of the balloon as described above, if desired.

Each electrode may be coupled to a separate electrically conductive wire (not shown) that extends along the inner or outer surface of the balloon for performing mapping and ablation functions. Examples of mapping catheters for use with medical ablation systems may be found, for example, in U.S. Patent Publication Nos. 2008/0249518 and 2002/0177765, both of which are hereby incorporated by reference in their entirety. As mapping electrodes, each wire may be electrically coupled to the input of an electrical activity processing system (not shown), such as, for example, an electromyograph. Each electrode may be assigned an electrode location and an electrode channel within the electrical activity processing system. The electrical activity processing system may be configured to detect the intrinsic electrical activity of the cells comprising the tissue region that each of the electrodes is in contact with. The electrical activity processing system may then use the intrinsic electrical activity detected from each of the electrodes to provide a map of electrical activity throughout a given tissue region or organ. Based on this map, specific tissue regions exhibiting aberrant electrical activity as compared to the surrounding tissues may be identified. For example, the aberrant electrical activity may manifest as a region of elevated electrical activity compared to the surrounding (normal) tissue.

For use as ablation electrodes, each wire may also be electrically coupled to an energy source (not shown) configured to selectively deliver ablation energy to its respective electrode. For example, once a tissue region exhibiting elevated electrical activity has been identified, the electrode (s) that detected the elevated electrical activity may be selectively energized to focally ablate that tissue region. Various energy sources may be used to deliver thermal energy to the target tissue, including, for example, radiofrequency (RF) energy, irreversible electroporation (IRE energy), microwave electromagnetic energy, laser energy, and/or acoustic energy, among others. For example, the energy source may include a conventional RF power supply that operates at a frequency in the range from 200 KHz to 1.25 MHz, with a conventional sinusoidal or non-sinusoidal wave form. Suitable power supplies are capable of supplying an ablation current at a relatively low voltage, typically below 150V (peak-to-peak), usually being from 50V to 100V. Simultaneous delivery of ablation energy to 64 electrodes will require a generator capable of delivering approximately 640 W. This wattage may be achieved by connecting multiple generators, e.g., 64 generators with a capacity of 20 W in series. Power supplies capable of operating within these ranges are available from commercial vendors, such as RadioTherapeutics of San Jose, Calif. The balloon may be overinflated during ablation to the point of achieving full contact with the bladder wall across the entire balloon surface and the balloon may be repurposed during this step as a cooling element (e.g., cold saline may be used to cool down the bladder during ablation). This cooling function of the balloon may be useful during energy delivery to allow larger and/or deeper lesions to be produced while avoiding "charring" of the bladder wall.

Figure 3B:
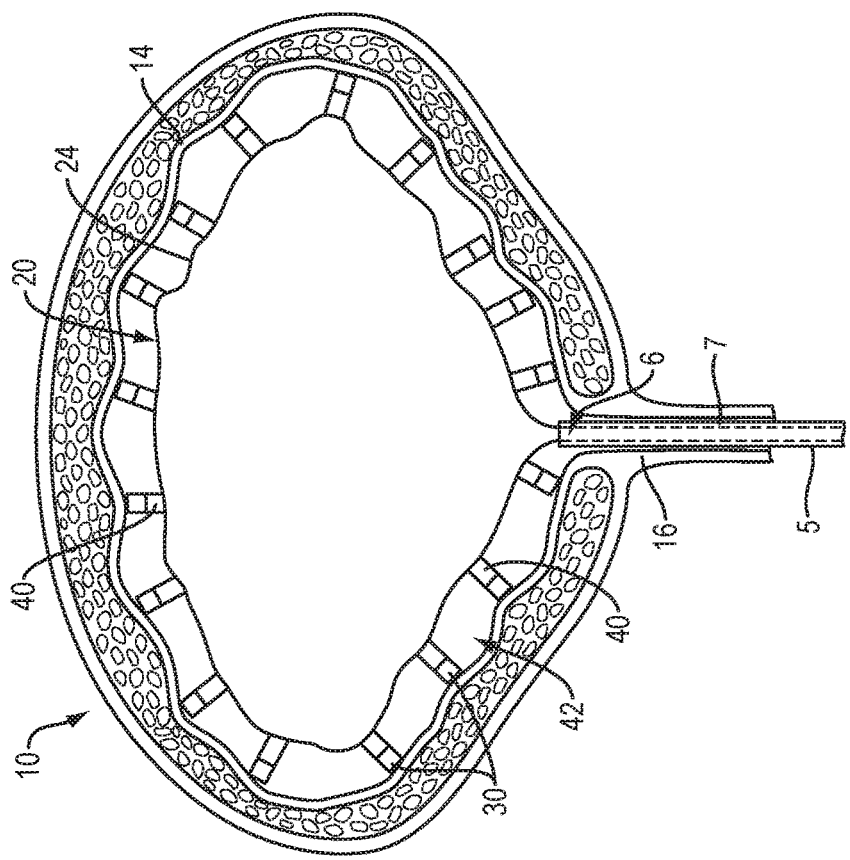
FIGS. 3A-D are cross-sectional views illustrating the steps involved in mapping and ablating a bladder using the balloon of FIG. 1. Following introduction of the balloon into the bladder (FIG. 3A) the balloon is expanded such that the electrodes are placed in contact with the bladder wall, and the bladder is flushed with saline (FIG. 3B). The mapping function of each electrode is used to identify local anatomical abnormalities (e.g., elevated electrical activity) within the bladder wall (FIG. 3C). The electrode(s) that detect a local anatomical abnormality are then energized to ablate the specific tissue region (FIG. 3D).
Figure 3A:
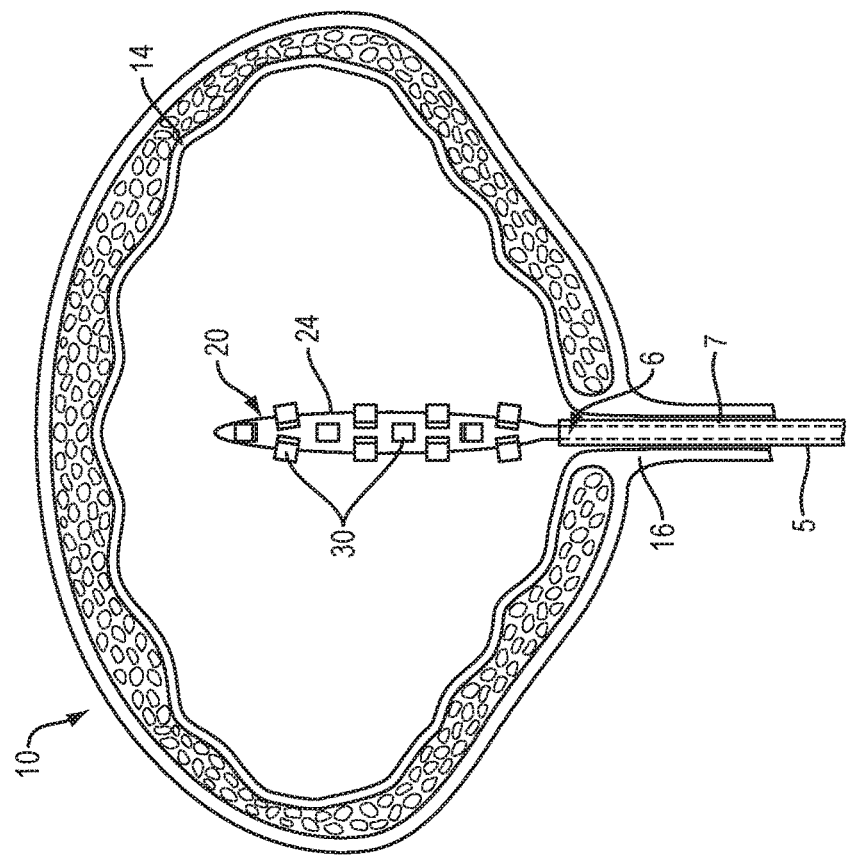
Figure 3C:
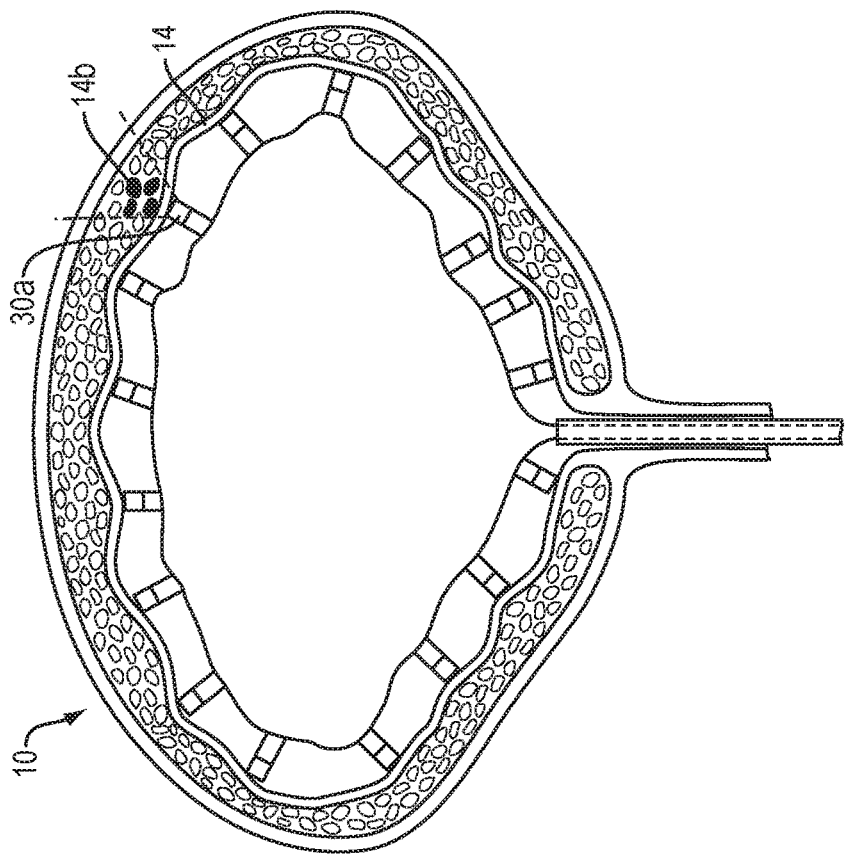

FIGS. 3A-3D illustrate the steps involved mapping and ablating the bladder wall 14 using an inflatable balloon like that of FIG. 1. The balloon 20 may be slidably disposed within the lumen 7 of a catheter 5 configured to be inserted through the urethra 16 into the bladder 10 of the patient. Once the catheter is properly positioned within the bladder 10, the collapsed balloon may be advanced beyond the distal end 6 of catheter 5 (FIG. 3A). In various embodiments, when in the collapsed configuration the balloon may have a profile (i.e., diameter) less than 3.7 mm, preferably less than 2.8 mm, and more preferably less than or equal to 2.5 mm. It will be appreciated that the balloon may be provided in a variety of different collapsed and expanded dimensions in order to treat a range of bladder sizes. In some embodiments, the catheter may be disposed within the lumen of an introducing element for introduction through the patient's urethra, including, for example, a cystoscope. Once properly positioned within the bladder, the balloon is inflated by introducing pressurized liquid or gas from a fluid source (not shown) into the interior region of the balloon body. The fluid or gas exerts pressure within the balloon body to urge the balloon from a collapsed configuration to an expanded configuration. The balloon is expanded such that it conforms to inner dimensions of the bladder, thereby placing each of the electrodes 30 on the outer surface of the balloon 20 into contact with the tissues of the bladder wall 14 (FIG. 3B). Continued exertion of pressure from the fluid or gas maintains the balloon body in the expanded configuration such that the electrodes remain in contact with the tissues of the bladder wall. In one embodiment, the fluid or gas may be continuously or intermittently circulated through the balloon body to maintain the balloon body in its expanded configuration. The spacers 40 ensure that the outer surface 24 of the balloon 20 do not contact the tissues of the bladder wall 14. An electrically conductive fluid, such as saline, is then infused into the space 42 between the outer surface of the balloon and the bladder wall. In one embodiment, the electrically conductive fluid is introduced from a separate tube (not shown) that runs along the outside of the balloon catheter to the fluid source. In another embodiment, a portion of the balloon body may be fluid permeable such that the fluid used to expand the balloon continuously flows from the interior region of the balloon to occupy the space between the outer surface of the balloon and the bladder wall.

Figure 3D:
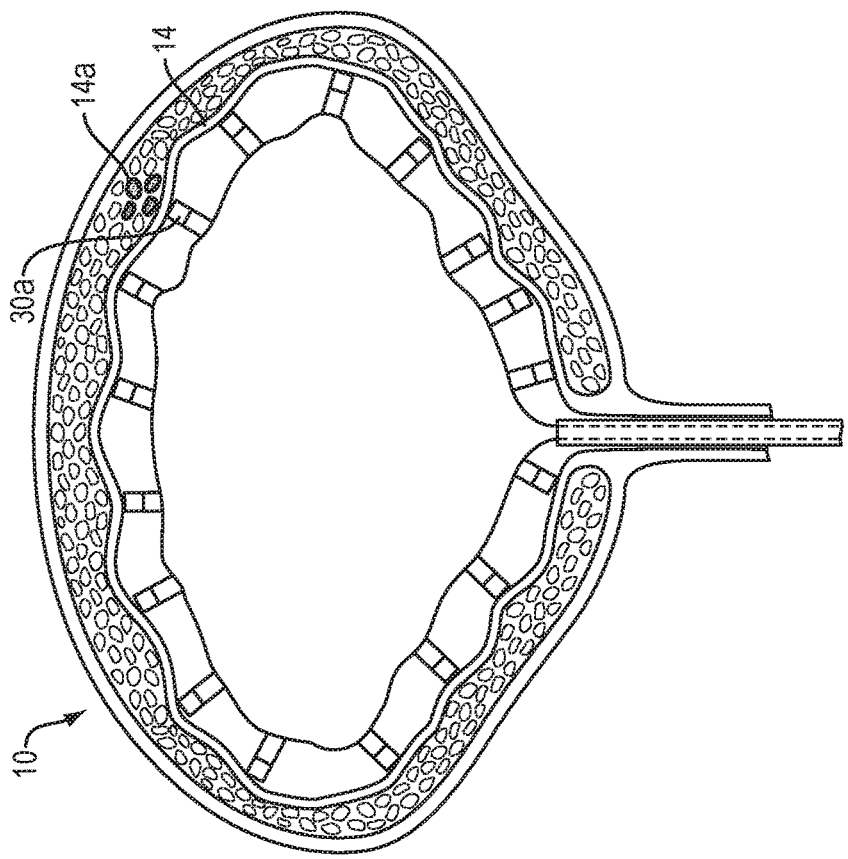

With the balloon properly expanded within the bladder, the mapping function of each electrode may be activated to sense/detect the intrinsic electrical activity of the tissue region they are in contact with. Once a tissue region of the bladder wall exhibiting elevated electrical activity 14a has been identified (FIG. 3C), ablation energy is selectively delivered from the energy source to the electrode(s) 30a that sensed the elevated electrical activity (FIG. 3D). This focal delivery of ablation energy causes the electrically overactive cell(s) of the identified tissue region to be heated to the point of cell death 14b, thereby creating scar tissue that is incapable of conducting electrical impulses.

The duration and/or intensity of the ablation energy may vary as necessary to achieve a satisfactory reduction of the elevated electrical activity. For example, ablation energy may be provided as a pulse, or series of pulses, of RF energy. The mapping function of the electrodes 30 may then be re-established to determine if the identified tissue region continues to exhibit elevated electrical activity. In the event that the electrical activity within such sites remains elevated, the selected tissue region may be re-energized with ablation energy. This process may be repeated as necessary until the tissue region exhibits a desired level of electrical activity. The ability of the inflatable balloon and attached electrodes to repeatedly monitor and ablate regions of the bladder wall ensures that focal energy is delivered only to the target region, and without prolonging the duration or intensity of the energy. This targeted approach not only focuses the energy on the selected regions in need of ablation, but minimizes or eliminates unwanted and potentially harmful ablation of surrounding healthy/normal tissues.

While the tissue region identified (FIG. 3C) and ablated (FIG. 3D) is in direct contact with one of the electrodes, it should be appreciated that the target tissue may lie next to or between one or more of the electrodes disposed about the outer surface of the balloon. In this situation, one or more of the electrodes in the vicinity of the target tissue may be energized such that the zone of ablation energy reaches (i.e., overlaps with) the target tissue.

Once the mapping function of the electrodes has verified that the ablated tissue region no longer exhibits elevated electrical activity, the balloon is returned to the collapsed configuration by removing the liquid or gas inflation medium from the interior region of the balloon body. The balloon may then retracted into the lumen of the catheter and withdrawn through the urethra.

Figure 4A:
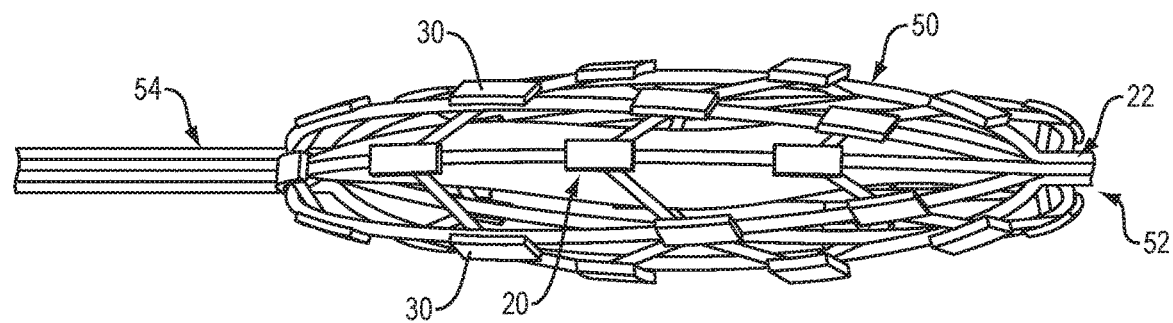
FIG. 4A is a side view of an expandable framework with attached electrodes that is free-floating over the surface of a balloon in a collapsed configuration, according to another embodiment of the present disclosure.
Figure 4B:
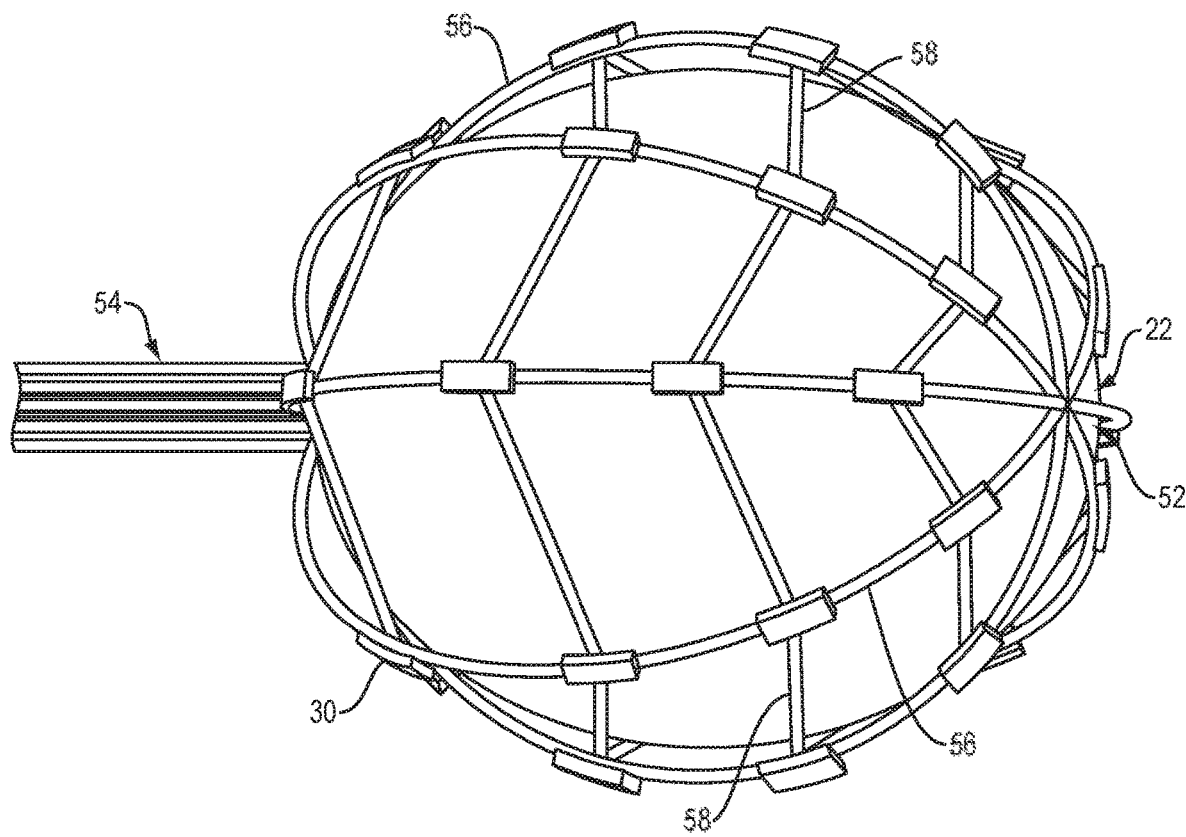
FIG. 4B is a side view of the expandable framework and balloon of FIG. 4A, with the balloon and expandable framework in an expanded configuration.

Because there is significant variation in size and shape between individual's bladders, a compliant balloon material is desirable in some embodiments in order to contact various surfaces. Unlike non-compliant balloons, compliant balloons are composed of materials that do expand to a single pre-determined volume, but may preferably expand to a volume in the range of 10% to 800% and more, and more preferably in the range of 50% to 200% compared to a non-compliant balloon with a similar uninflated volume. Examples of compliant balloon materials include elastomers such as silicone rubber, ethylene-propylene-diene copolymers, butyl rubber, styrene-isobutylene-styrene copolymers, urethanes, and latexes, among others. However, where printed circuit technology is employed, such materials may cause issues of adhesion of the electrodes to the balloon. One way to address this issue is illustrated in FIGS. 4A-B, wherein a schematic view of an embodiment of a medical device is shown that includes an expandable-collapsible framework 50 (i.e., grid or mesh-like structure) that is free-floating about the outer surface of an inflatable balloon 20 such that the framework 50 expands as the underlying balloon moves from a collapsed configuration (FIG. 4A) to an expanded (FIG. 4B). The only attachment point between the framework 50 and balloon 20 is at their respective distal ends 52, 22 to ensure that the framework 50 remains free-floating about the balloon 20. As the balloon 20 moves into an expanded configuration, the outer surface of the balloon 20 contacts the inner surface of framework 50, thereby urging the framework 50 to likewise expand. As the balloon 20 moves from an expanded to collapsed configuration, the framework 50 may be collapsed by applying tension to (i.e., pulling) a proximal end 54 of the framework in a direction away from the attached distal ends 22, 52 of the balloon and framework. A plurality of electrodes 30 are carried about the outer surface of the framework 50. A spacer (not shown) may be placed between the outer surface of the framework 50 and each electrode 30 to ensure that the electrodes are raised above and extend outward from the surface of the framework 50 and underlying balloon 20. The spacers may be attached to the outer surface of the framework using, by way of non-limiting example, a glue, a weld, a UV-curable acrylate resin or other suitable adhesive. The spacers may be used to elevate the electrodes above the outer surface of the framework to improve contact between each electrode and the tissues of the bladder wall when the balloon and framework are in the expanded configuration. In one embodiment, each spacer may include a pressure sensor configured to provide pressure feedback when the electrode is in contact with the bladder wall. An individual pressure sensor may be used for each individual spacer, such that pressure feedback information is obtained for each electrode. The spacers also allow saline, or other suitable electrically conductive fluid, to be irrigated around the outer surface of the balloon and framework to hydrate the bladder and provide a consistent interface between the bladder wall and each electrode 30. This allows for improved electrical conductivity between the tissues of the bladder wall and each electrode for more reliable mapping and ablation.

As discussed above, the balloon may be designed to conform to the specific shape of an individual patient's bladder prior to performing the mapping/ablation procedure. Similarly, the balloon may be formed of a flexible and non-compliant material such that it expands to conform the framework to the bladder lumen but does not over-expand, thereby leaving a space between the outer surface of the balloon and the bladder wall for the infused saline to fill.

The balloon may be coated, using a variety of materials, in order to enhance a specific property. These coatings would generally cover only the balloon surface, and not the electrodes, although if the coating were conductive, it could also cover the electrodes. Examples of coating uses include lubricious coatings, abrasion and puncture resistant coatings, or tacky coatings. Lubricious coatings include those commonly used in medical devices, such as polyvinylpyrrolidone, polyacrylic acid copolymers, hyaluronic acid, polyurethanes, combinations of the above, commonly known to those practiced in the art. These coatings may also have primer layers to improve adhesion to the balloon.

As best illustrated in FIG. 4B, in one embodiment, the framework includes a proximal end 54 and a distal end 52, between which flexible splines 56 extend in a circumferentially spaced relationship. The framework may take the form basket that defines an interior space when in the expanded configuration. The splines may be made from a resilient inert material, such as nitinol, acrylate-based polymers, polyurethane-based polymers, polynorbornene-based polymers, polypropylene, polyethylene, polycarbonates, nylons, PEEK, polylactide-based polymers, platinum, tungsten, titanium, stainless steel, nickel and any combinations thereof. The splines 56 may be connected between the proximal and distal ends in a pre-tensed condition to bend and conform to the shape of the underlying balloon 20. The embodiment depicted in FIGS. 4A-4B includes five splines 56 that form the 3-D structure. Each spline is connected to the adjacent splines by a series of four struts 58. Additional or fewer splines connected by additional or fewer struts may be used in other embodiments. An electrode 30 is attached at the intersection of each spline 56 and strut 58, such that a total of 20 electrodes are positioned equidistantly about the outer surface of the framework in the embodiment shown. While an arrangement of 20 mapping electrodes is shown disposed on the framework, the mapping electrodes may alternatively be arranged in different numbers, on different structures, and/or in different positions. Each electrode is typically coupled to a separate electrically conductive wire (not shown) that extends along the inner or outer surface of the framework for performing mapping and ablation functions, as discussed above.

Figure 5A:
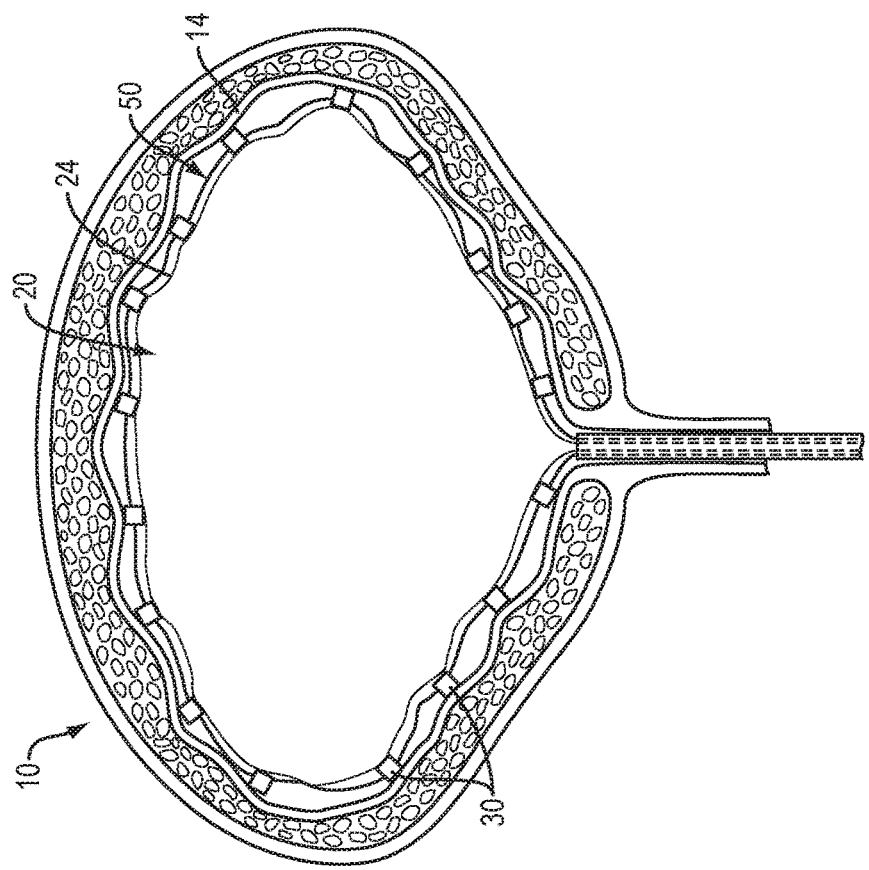
FIGS. 5A-D are cross-sectional views illustrating the steps involved in mapping and ablating a bladder using the expandable framework and balloon of FIGS. 4A-B. Following introduction of the expandable framework and balloon into the bladder (FIG. 5A), the balloon is expanded such that the expandable framework free-floating about the surface of the balloon also expands, thereby placing the electrodes in contact with the bladder wall (FIG. 5B). After the bladder is flushed with saline, the mapping function of each electrode is used to identify local anatomical abnormalities (e.g., elevated electrical activity) within the bladder wall (FIG. 5C). The electrode(s) that detect a local anatomical abnormality are then energized to ablate the specific tissue region (FIG. 5D).
Figure 5B:
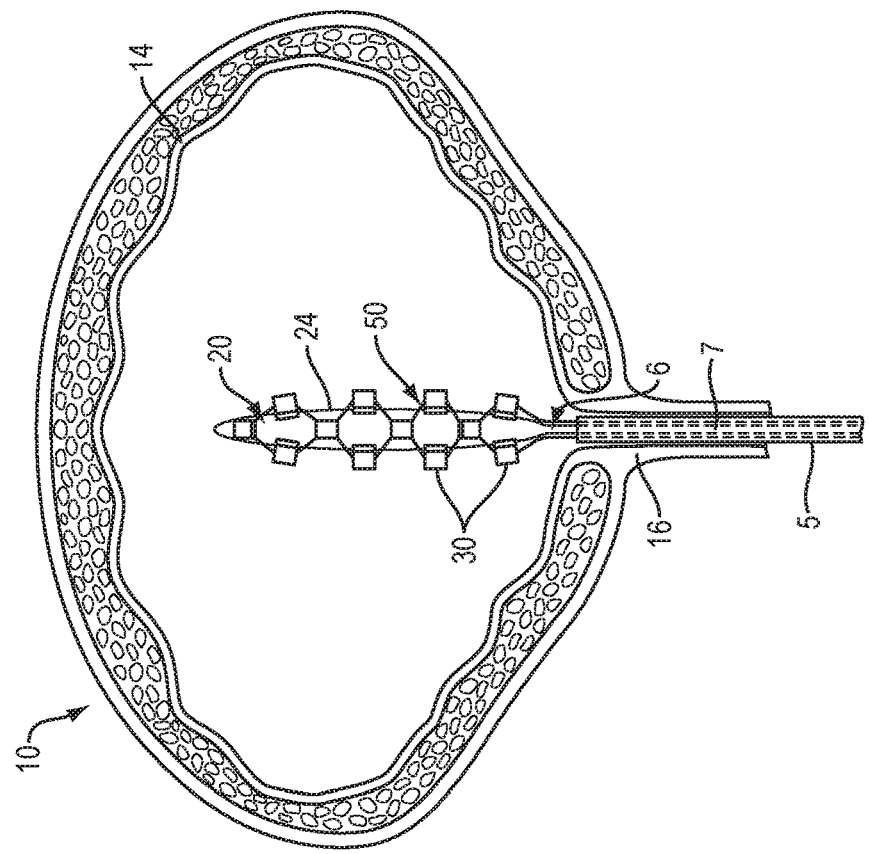

FIGS. 5A-5D outline the steps involved in mapping and ablating the bladder wall using an inflatable balloon and framework like that of FIGS. 4A-4B. The balloon 20 and framework 50 may be slidably disposed within the lumen 7 of a catheter 5 configured to be inserted through the urethra 16 into the bladder 10 of the patient. Once the catheter is properly positioned within the bladder, the unexpanded balloon 20 and framework 50 may be advanced distally beyond the distal end 6 of the catheter 5 (FIG. 5A). In various embodiments, when in the collapsed configuration the balloon 20 may have a profile (i.e., diameter) less than 3.7 mm, preferably less than 2.8 mm, and more preferably less than or equal to 2.5 mm. It will be appreciated that the balloon may be provided in a variety of different collapsed and expanded dimensions in order to treat a range of bladder sizes. In some embodiments, the catheter may include a variety of introducing elements, including, for example, a cystoscope. Once properly positioned within the bladder 10, the balloon 20 is inflated by introducing pressurized liquid or gas from a fluid source (not shown) into the interior region of the balloon body. The fluid or gas exerts pressure within the balloon body to urge the balloon from a collapsed configuration to an expanded configuration. As the balloon expands the framework 50 floating about the outer surface of the balloon expands accordingly, placing the electrodes 30 of the framework 50 in contact with the tissues of the bladder wall 14 (FIG. 5B). Continued exertion of pressure from the fluid or gas maintains the balloon body in the expanded configuration such that the electrodes remain in contact with the tissues of the bladder wall. In one embodiment, the fluid or gas may be continuously or intermittently circulated through the balloon body to maintain the balloon body in its expanded configuration. An electrically conductive fluid, such as saline, is then infused into the space between the outer surface of the balloon and the bladder wall. In one embodiment, the saline solution is introduced from a separate tube (not shown) that runs along the outside of the balloon catheter to a fluid source. In another embodiment, a portion of the balloon may be fluid permeable such that a portion of the fluid used to expand the balloon continuously flows from within the balloon to fill the space between the outer surface of the balloon and the bladder wall. The balloon may be repurposed during this step as a cooling element (e.g., cold saline may be used to cool down the bladder during ablation). This cooling function of the balloon may be useful during energy delivery to allow larger and/or deeper lesions to be produced while avoiding "charring" of the bladder wall.

Figure 5D:
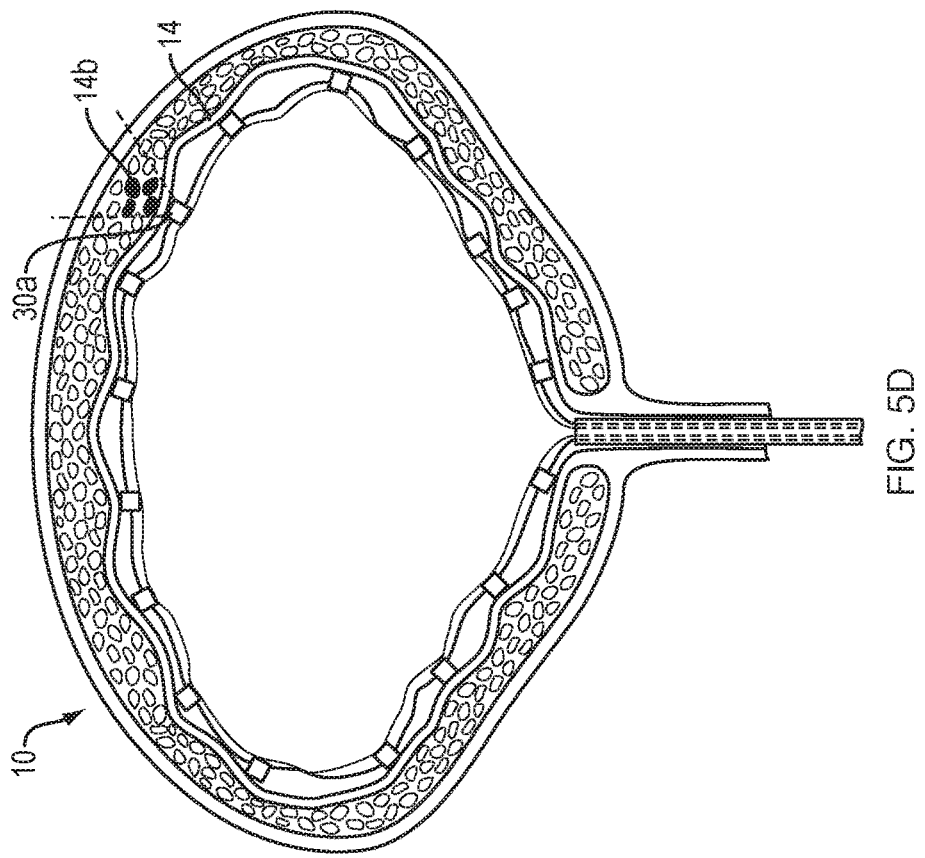
Figure 5C:
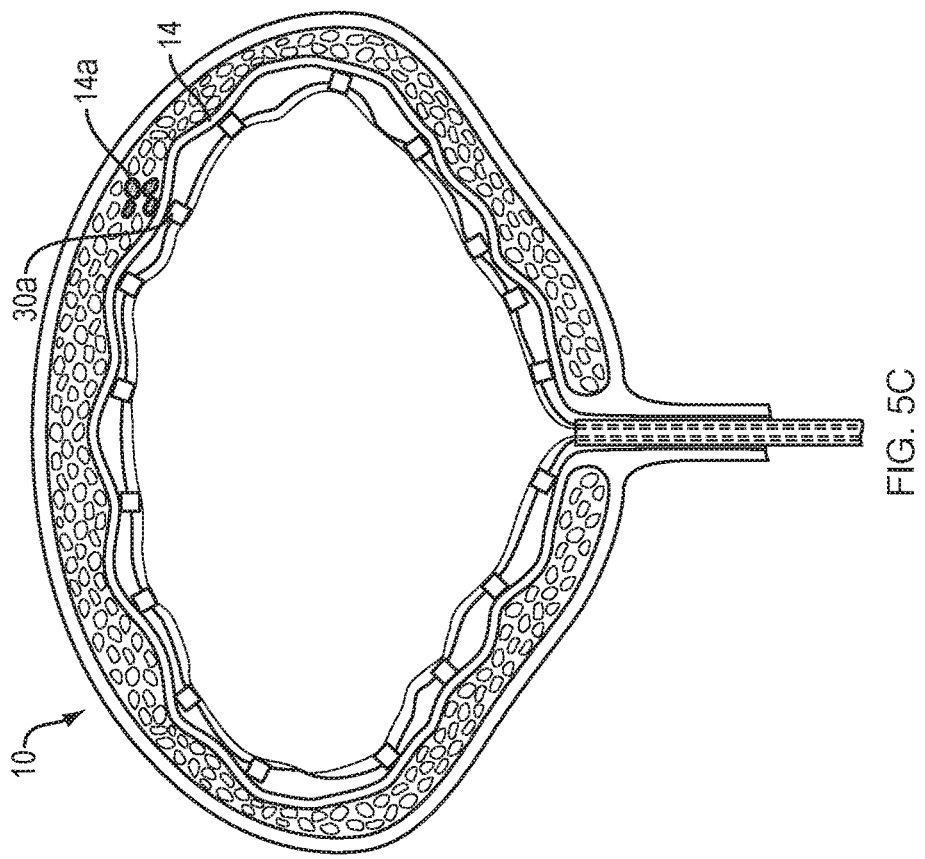

With the balloon 20 properly expanded within the bladder 10, the mapping function of each electrode 30 is activated to sense/detect the intrinsic electrical activity of the tissue region that they are in contact with. Once a tissue region of the bladder wall exhibiting elevated electrical activity has been identified 14a (FIG. 5C), ablation energy is selectively delivered from the energy source to the electrode(s) 30a that sensed the elevated electrical activity (FIG. 5D). This focal delivery of ablation energy causes the electrically overactive cell(s) of the identified tissue region to be heated to the point of cell death, thereby creating scar tissue that is incapable of conducting electrical impulses.

While the present disclosure relates generally to the application of thermal ablation energy to the target tissues identified by the mapping electrodes, it should also be appreciated the non-lethal energy, such as electrically stimulating energy or delivery of therapeutic agents through electroporation, may be administered to restore normal electrical activity to the cells of the target tissue.

What is claimed is:

1. A medical device, comprising:
   a balloon configured to move between a collapsed configuration and an expanded configuration;
   an expandable-collapsible framework comprising a plurality of flexible splines and struts disposed about an outer surface of the balloon, wherein a distal end of the framework is attached to a distal end of the balloon such that the struts and splines are free-floating about the balloon; and
   a plurality of electrodes carried about an outer surface of the framework, each of the plurality of electrodes positioned at an intersection of a flexible spline and strut of the plurality of flexible splines and struts.

2. The medical device of claim 1, wherein each of the plurality of electrodes extends outward from the surface of the framework.

3. The medical device of claim 1, further including a spacer disposed between the outer surface of the framework and one of the plurality of electrodes.

4. The medical device of claim 1, wherein each of the plurality of electrodes is electrically coupled to an ablation energy source.

5. The medical device of claim 1, wherein each of the plurality of electrodes is electrically coupled to an electrical activity processing system.

6. The medical device of claim 1, wherein each of the plurality of electrodes includes a sensing electrode, a mapping electrode, a stimulating electrode or an ablation electrode.

7. The medical device of claim 1, wherein a lumen of the balloon is in fluid communication with a fluid source, wherein the balloon moves from the collapsed configuration to the expanded configuration by flowing a fluid from the fluid source into the lumen of the balloon.

8. A medical device, comprising:
a balloon configured to move between a collapsed configuration and an expanded configuration;
an expandable-collapsible framework comprising a plurality of flexible splines and struts disposed about an outer surface of the balloon, wherein the flexible splines are configured to bend and conform to the shape of the balloon in the expanded configuration, and wherein a distal end of the framework is attached to a distal end of the balloon such that the struts and splines are free-floating about the balloon; and
a plurality of electrodes carried about an outer surface of the framework, each of the plurality of electrodes positioned at an intersection of a flexible spline and strut of the plurality of flexible splines and struts.

9. The medical device of claim 8, wherein each of the plurality of electrodes extends outward from the surface of the framework.

10. The medical device of claim 8, further including a spacer disposed between the outer surface of the framework and one of the plurality of electrodes.

11. The medical device of claim 8, wherein each of the plurality of electrodes is electrically coupled to an ablation energy source.

12. The medical device of claim 8, wherein each of the plurality of electrodes is electrically coupled to an electrical activity processing system.

13. The medical device of claim 8, wherein each of the plurality of electrodes includes a sensing electrode, a mapping electrode, a stimulating electrode or an ablation electrode.

14. The medical device of claim 8, wherein a lumen of the balloon is in fluid communication with a fluid source, wherein the balloon moves from the collapsed configuration to the expanded configuration by flowing a fluid from the fluid source into the lumen of the balloon.

* * * * *